US010023358B2

(12) United States Patent
Carrel

(10) Patent No.: US 10,023,358 B2
(45) Date of Patent: Jul. 17, 2018

(54) PACKAGING FOR CONTAINERS

(75) Inventor: Franck Carrel, Pont de Claix (FR)

(73) Assignee: Becton Dickinson France S.A.S., Le Pont de Claix (FR)

( * ) Notice: Subject to any disclaimer, the term of this patent is extended or adjusted under 35 U.S.C. 154(b) by 0 days.

(21) Appl. No.: 13/978,883

(22) PCT Filed: Jan. 11, 2012

(86) PCT No.: PCT/IB2012/050137
§ 371 (c)(1),
(2), (4) Date: Jul. 10, 2013

(87) PCT Pub. No.: WO2012/095800
PCT Pub. Date: Jul. 19, 2012

(65) Prior Publication Data
US 2013/0284632 A1    Oct. 31, 2013

(30) Foreign Application Priority Data

Jan. 12, 2011   (EP) .................................... 11305030

(51) Int. Cl.
*B65D 21/00* (2006.01)
*B65D 21/04* (2006.01)
*A61M 5/00* (2006.01)

(52) U.S. Cl.
CPC ............. *B65D 21/04* (2013.01); *A61M 5/008* (2013.01); *B65D 21/045* (2013.01)

(58) Field of Classification Search
CPC .. B65D 21/04; B65D 21/045; B65D 21/0234; B65D 21/0233; B65D 21/083; B65D 21/086; B65D 85/62; A61M 5/008; A61M 5/002; A61B 19/0275; A61B 2119/0275; F25D 3/08; F25D 3/06

USPC ....... 206/507, 505, 511, 506, 518, 509, 571, 206/364, 365, 370, 564, 449, 563; 220/569.2

See application file for complete search history.

(56) References Cited

U.S. PATENT DOCUMENTS 3,420,402 A * 1/1969 Frater et al. .................. 206/507
3,643,812 A * 2/1972 Mander ..................... B01L 9/06
206/443

(Continued)

FOREIGN PATENT DOCUMENTS

EP         1449551 A1    8/2004
WO     2010122129 A1   10/2010

*Primary Examiner* — Anthony Stashick
*Assistant Examiner* — James M Van Buskirk
(74) *Attorney, Agent, or Firm* — The Webb Law Firm

(57) ABSTRACT

This packaging is for containers having each a cylindrical body and an upper surface located at or near an extremity of the body, said packaging comprising a nest, a tub and a sealing cover; the nest having a nesting structure to receive the containers and comprising at least one first supporting surface, to be received on at least one corresponding supporting surface of the tub, the tub having a bottom wall, lateral walls forming an upper opening, and a peripheral flange leveled with said upper opening, for the sealing of said sealing cover thereon; said nest includes at least one second supporting surface rigidly connected to said at least one first supporting surface and so positioned with respect to this at least one first supporting surface that this second supporting surface is located, when the nest is placed in the tub, at the level of said peripheral flange.

17 Claims, 5 Drawing Sheets

(56) References Cited

U.S. PATENT DOCUMENTS

| | | | | |
|---|---|---|---|---|
| 3,734,341 | A | * | 5/1973 | Levenhagen ........ B65D 21/045 |
| | | | | 206/507 |
| 4,974,737 | A | * | 12/1990 | Miller .......................... 220/4.03 |
| 5,316,172 | A | * | 5/1994 | Apps .................. B65D 21/0212 |
| | | | | 220/519 |
| 5,465,843 | A | * | 11/1995 | Koefelda ...................... 206/507 |
| 5,704,485 | A | * | 1/1998 | Cautereels et al. ........... 206/546 |
| 5,752,602 | A | * | 5/1998 | Ackermann et al. ......... 206/507 |
| 6,164,044 | A | * | 12/2000 | Porfano .................. B65B 55/10 |
| | | | | 422/28 |
| 6,722,054 | B2 | * | 4/2004 | Yarborough et al. ........... 34/284 |
| 7,721,891 | B2 | * | 5/2010 | Dubois ......................... 206/507 |
| 2012/0045311 | A1 | | 2/2012 | Lepot |

* cited by examiner

PACKAGING FOR CONTAINERS

BACKGROUND OF THE INVENTION

Field of the Invention

This invention is directed to a packaging for containers such as, for example, syringes or cartridges. Each container notably comprises a cylindrical body, in particular tubular, and "upper surface" located at or near the proximal end of this cylindrical body. This upper surface is generally formed by a flange that can be integrally formed with the cylindrical body or that can be a separate piece mounted on this body.

In this application, the distal end of a component or of a device means the end furthest away from the hand of the user and the proximal end means the end closest to the hand of the user, when the component or device is in the use position. Similarly, in this application, the terms "in the distal direction" and "distally" mean in the direction of the injection, and the terms "in the proximal direction" and "proximally" mean in the direction opposite to the direction of injection.

Discription of Related Art

Often, the containers must be transported from one site to another, when they are manufactured in one site and filled in another site, or, less frequently, when they are manufactured and filled in the same site and must be delivered, once filled, to another site.

For this transportation, the containers are usually put in a "global packaging" comprising a grouping tray or nest, hereinafter "nest", a packaging tub, hereinafter "tub", a sealing cover and a plastic bag, hereinafter "header bag" to insure the sterility. The combination of the nest, the tub and the sealing cover will be cited hereinafter as "packaging" while the tub will correspond to an empty tub.

The nest can have various shapes according to the type of containers received: it can comprise openings made through the nest, along the thickness thereof, i.e. these openings extending from an upper surface of the nest to a lower surface thereof. The openings that can be or not coaxially surrounded by chimneys for receiving the cylindrical bodies of the containers with flanges, these flanges leaning on the upper ends of the chimneys. With this kind of nest, cylindrical bodies with flanges (e.g. syringes) are loaded via the upper surface of the nest in order to position them into the openings of such nest. Alternatively, the nest can have specific openings for receiving cartridges that would be in contact with the bottom of the tub. In another embodiment, the nest can have chimneys with closed bottoms for receiving containers without flanges; the nest can also be made in a resilient material and have openings in which the containers are frictionally maintained. In the following description, the nest described is the one with openings coaxially surrounded by chimneys for receiving containers with flanges.

The tub includes a peripheral outer flange levelled with its upper opening, for the sealing of the sealing cover. In use, the nest is placed into the tub which is sealed with a sealing cover and sterilised. Then, series of global packagings are stacked into a box, bottom up, for example, a cardboard or a plastic box with an intermediate sheet placed between two series of global packagings, a series being defined as a row of several global packagings.

The header bag can be a classical header bag (e.g. made of plastic including a porous part). Alternatively, the header bag can have a reinforced part positioned in such manner that the header bag gets a function of load spreader. This reinforced part can be interdependent or not with the bag, it can be in moulded or thermoformed plastic, and it can be placed inside or outside the header bag. This reinforced part can be for example at least one thermoformed plastic plate placed inside the bag below and/or above the tub. This reinforced load spreader header bag protects the containers packaged into the packaging.

When received at destination, the global packagings are extracted from the box and flipped bottom down, the header bag is open, the tub is extracted from the header bag and unsealed. Then, the nests are extracted therefrom and the containers can be filled and/or handled.

Said intermediate sheet is used for distributing the load of an upper series of global packagings on the lower series of global packagings. However, when global packagings are stacked without the intermediate sheet between them to, a load is exerted on the sealing cover of the global packagings. This load can generate a contact of the sealing cover with the containers flanges, and then generate contaminating particles on the containers or lead to the breakage of the flanges.

In addition, the containers user, after removing the global packagings from the box, may want to store some packagings or global packagings and will therefore need to stack them. This may also bring the sealing cover in contact with the flanges of the containers and generate contamination or breakage of the flanges in the same way.

Furthermore, this kind of packaging has the drawback of consuming a large amount of packaging materials, because only fifteen global packagings can be placed in a same box (five stacked series of three global packagings in width, each series being separated one from another by an intermediate sheet) and because intermediate sheets are required. For the containers users, opening many boxes and removing many intermediate sheets is burdensome and time-consuming.

The purpose of the present invention is to overcome these drawbacks.

The main object of the invention is therefore to provide a packaging like described above, which efficiently prevents from any contamination or breakage of the containers flanges when a number of packagings or global packagings are stacked.

Another goal of the invention is to provide a global packaging which reduces the amount of packaging materials used for transportation and give rise to an easier work for opening the box containing these packagings.

SUMMARY OF THE INVENTION

The packaging concerned comprises, in a way known per se, a nest, a tub and a sealing cover, the nest comprising at least one first supporting surface, to be received on at least one corresponding supporting surface of the tub, and the tub having a bottom wall, lateral walls forming an upper opening, and a peripheral flange levelled with said upper opening, for the sealing of said sealing cover thereon.

According to the invention, said nest have receiving means for receiving the containers (2) and comprises at least one second supporting surface rigidly connected to said at least one first supporting surface and so positioned with respect to this at least one first supporting surface that this second supporting surface is located, when the nest is placed in the tub, at the level of said peripheral flange.

"At the level of said peripheral flange" must be understood as meaning that said second supporting surface can be precisely in the same plane than said peripheral flange, or just below it or just above it.

The applicant has found that the contamination or the breakage of the containers occurs, when packagings of the prior art are stacked, due, in part, to an insufficient distribution of the load of the upper packaging(s) on the lower packaging. Indeed, this load is not only supported by the sealing cover but also by the upper surface of the containers. This insufficient distribution of the load leads to the limitation of the number of global packagings to be stacked in a same box. Furthermore, in order to solve the problem of the load, intermediate sheets are placed in the box between each layer of three global packagings in order to improve the distribution of said load. However, the use of such intermediate sheets leads to an increase of the amount of the packaging materials and to additional work when opening a large number of boxes containing these global packagings.

The nest according to the invention has at least one second supporting surface which provides additional distribution of the load when packagings are stacked since specific parts of the bottom of an upper tub rely on said second supporting surface of the nest. Additionally, said at least one second supporting surface provides support to the sealing cover, thus reducing or avoiding the possibility of contact between the sealing cover and containers.

Preferably, the nest comprises two second supporting surfaces on two opposed sides, notably on the lateral sides thereof.

It can also comprise a said second supporting surface on the middle portion thereof.

Preferably, said receiving means comprise openings.

When the containers have flanges at their proximal ends and when said receiving means comprise chimneys in which the containers are intended to be inserted with the flanges thereof bearing on the upper ends of said chimneys, said second supporting surfaces define a first plane that is spaced apart from a second plane defined by said upper ends of said chimneys, the distance between said first plane and said second plane being superior to the thickness of the flanges of the containers.

Preferably, said lateral walls of the tub are sloped inwardly from said upper opening to said bottom wall, so that, when a first tub is stacked on a second, identical, tub having a nest therein, the contour of the bottom wall of said first tub is within the contour of the upper opening of said second tub, and said second supporting surfaces are so located that the bottom wall of said first tub bears thereon.

Said second supporting surfaces distribute the load of the upper tub(s) when tubs are stacked on the lateral walls of the lower tub(s) of this stack, through the nest. In this way, the sealing covers or the containers of the lower tubs are no longer supporting any load of the upper tubs. As a result, much more than five tubs in height can be stacked in a box and the intermediate sheets can be removed. Additionally, with such nest, the risk of contamination or deterioration of the containers can be avoided even if a large number of packagings are stacked.

Furthermore, at least two identical empty tubs can thus be nested one in another before putting the nests in them. This provides an advantageous space saving for the container manufacturer. This also provides an advantageous space saving for the containers user, who can nest tubs after removal of the nests therefrom.

Each second supporting surface can comprise a rounded inner longitudinal edge.

This rounded edge reduces and even eliminates the risk of generation of particles on the containers.

Each second supporting surface comprises a smooth part that is sized and shaped to form a gripping surface for receiving a tool able to grasp automatically the nest.

Said second supporting surfaces are preferably integrally formed within the nest.

Alternatively, said second supporting surfaces are additional pieces mounted on/or attached to the nest.

According to a preferred embodiment of the invention, each second supporting surface is formed by the upper wall of a supporting element, this supporting element having an inner lateral wall and an outer lateral wall, and said supporting element comprising interior walls connecting said inner lateral wall and said outer lateral wall, for strengthening said supporting element. Said interior walls can also be connected to said upper wall.

When the nest comprises tubular chimneys for receiving the containers, forming said receiving means, said inner lateral wall can have an undulated shape, formed of successive alternated protruding portions and depressed portions that follow the outline of the row of chimneys.

Preferably, the nest has notches for the insertion of user's fingers for grasping the nest. These notches are preferably delimited by walls providing increased contact surfaces for the user's fingers.

Each notch can have an abutment, notably a ridge, aimed at the gripping by one user's finger.

According to a preferred embodiment of the invention in this case, said tub comprises:
  recessed portions, each recessed portion forming, on the inner side of the tub, a supporting pillar with an upper supporting surface for receiving the nest, and
  recesses able to receive the supporting pillars of a second tub, thus allowing the nesting of two empty tubs.

The tub, according to the invention, thus provides supporting surfaces for receiving the nest that have limited areas, whereas the tub according to the prior art has continuous supporting surfaces for receiving the nest that form a continuous shoulder along the periphery of the tub. These supporting surfaces of limited areas let more space on the nest for receiving containers vertically, so an increased number of containers (120 instead of 100) can be placed in a same nest in a tub remaining of the same outer dimensions.

The tub can have said recessed portions on, at least, two opposed lateral walls or at the corners thereof.

Preferably, the tub comprises, in, at least, one of said recess, an abutting surface to block the upper supporting surface of a supporting pillar when two empty tubs are nested.

The invention will be better understood and other characteristics and advantages thereof will become evident, with reference to the attached schematic drawings, representing, by way of non-limiting and non-exhaustive example, a preferred embodiment of said packaging.

BRIEF DESCRIPTION OF THE DRAWINGS

FIG. 4 shows a packaging 1 for the transport of containers 2 (such container 2 can be seen on FIG. 8), comprising a nest 5, a tub 6, and a sealing cover 7.

DETAILED DESCRIPTION OF THE INVENTION

Each container 2 comprises a cylindrical body, in particular tubular, and an upper surface that can be a flange located at or near the proximal end of this cylindrical body.

Figure 1:
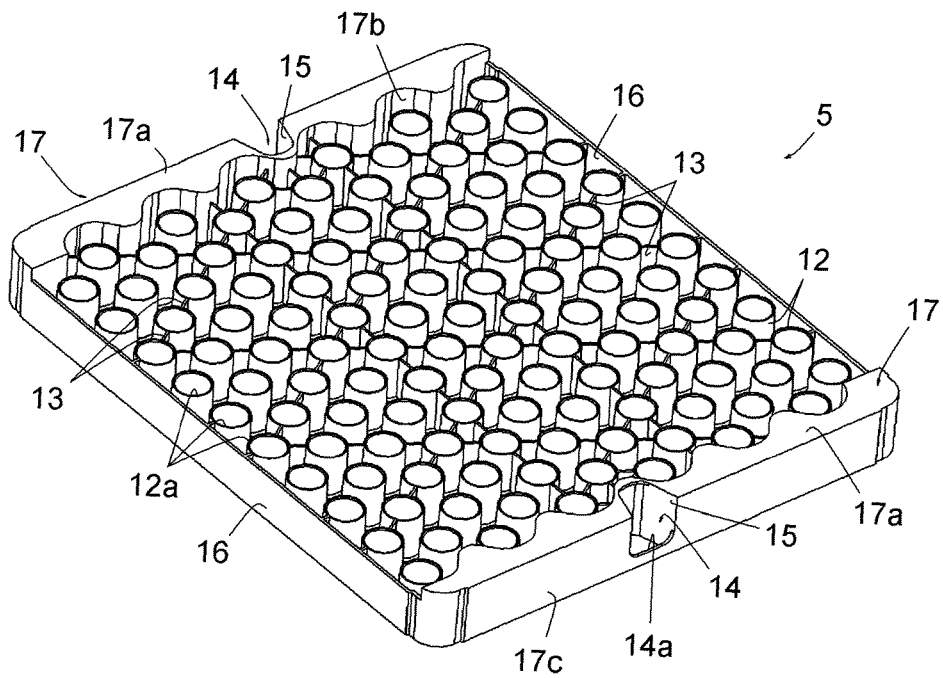
FIG. 1 is a perspective view of a nest that is part of the packaging, showing the upper side of this nest.
Figure 2:
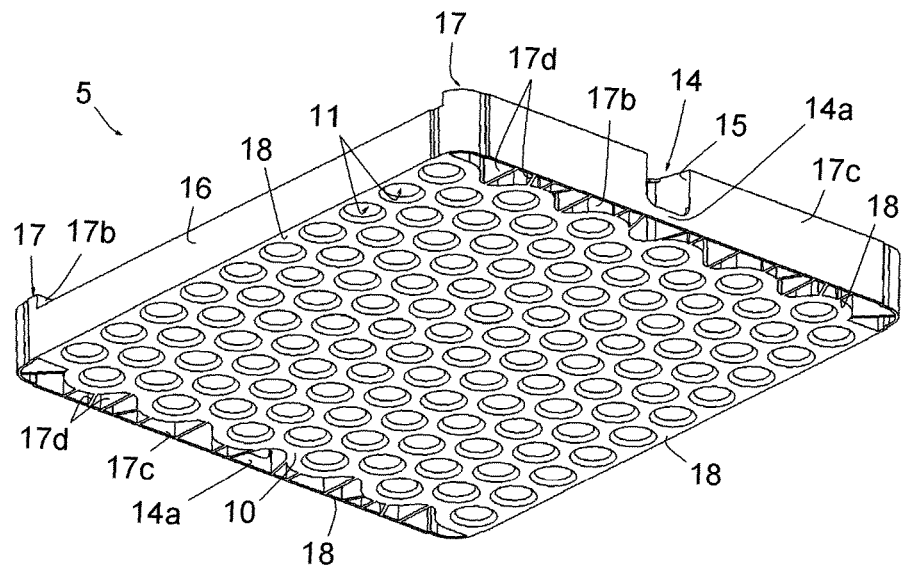
FIG. 2 is a view similar to FIG. 1, showing the lower side of this nest.
Figure 3:
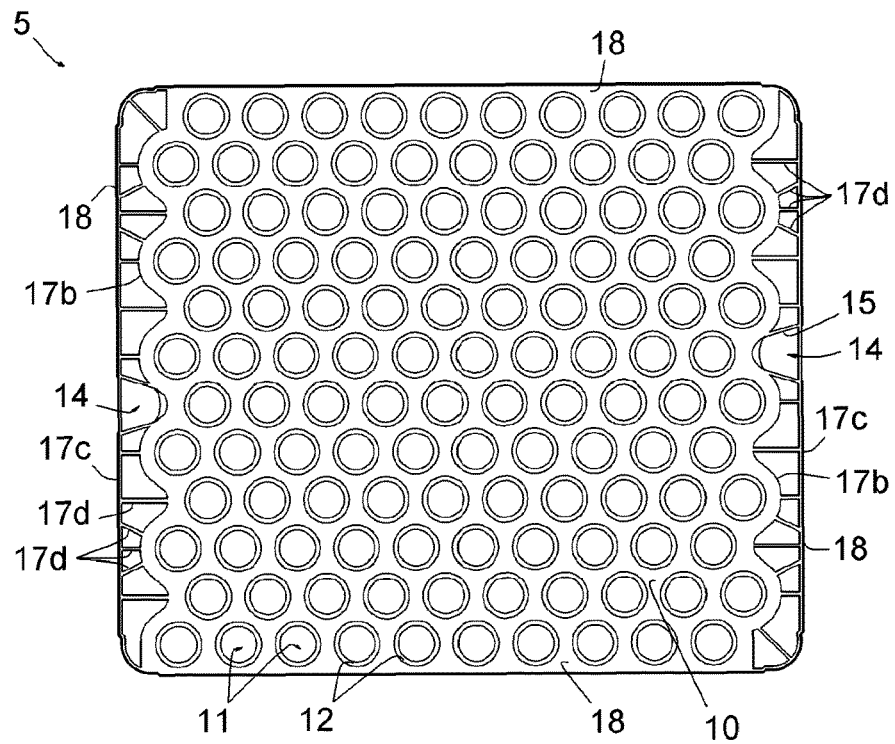
FIG. 3 is a top view of this lower side of the nest.

Referring more particularly to FIGS. 1-3, the nest 5 comprises a flat, substantially square or rectangular bottom wall 10, through openings 11 coaxially surrounded by chimneys 12, radial connection walls 13, notches 14 on first and second opposed edges of the bottom wall 10, walls 15 delimiting the notches 14, side walls 16 extending on third and fourth opposed edges of the bottom wall 10 that are perpendicular to said first and second edges, and two supporting elements 17 extending along said first and second opposed edges, along the portion of the nest comprising the chimneys. The nest 5 is formed by a single part of moulded plastic material.

The inferior edges of the supporting elements 17 and the edges of the bottom wall 10 form first supporting surfaces 18, intended to be received on corresponding supporting surfaces 26 of the tub 6, described below.

Figure 8:
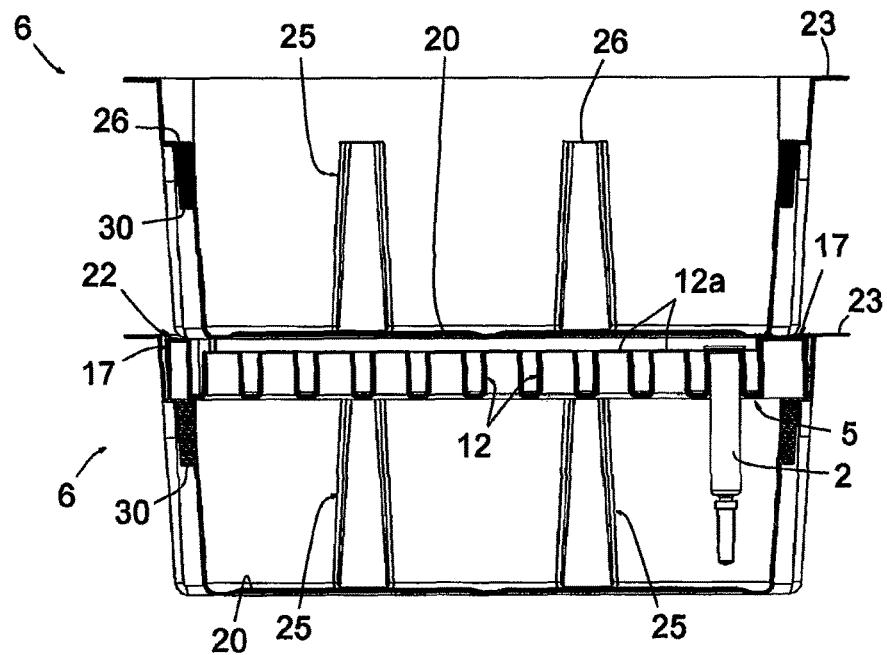
FIG. 8 is a cross-sectional view of said first and second tubs taken along the line VIII-VIII of FIG. 7, a syringe body being shown, placed on the nest of said second tub.

As shown on FIG. 8, the cylindrical bodies of the containers 2 are inserted in said chimneys 12 and through said openings 11 until the flanges abut the receiving surface 12a of the chimneys 12.

With reference to FIG. 2, some radial connection walls 13 connect some adjacent chimneys 12 one to each other and can also connect some chimneys 12 to the side walls 16 of the nest 5 for rigidifying the nest 5.

The notches 14 allow the insertion of a user's fingers, for grasping the nest 5, and the delimiting walls 15 provide increased contact surfaces for these fingers. Each notch 14 has a ridge 14a forming an abutment aimed at the gripping by one user's finger.

As it is described on FIG. 2, each supporting element 17 comprises an upper wall 17a, an inner lateral wall 17b, i.e. a wall located on the side of the nest 5 comprising the chimneys 12, an outer lateral wall 17c, on the opposed side, and interior walls 17d. All these different walls connected said upper, inner and outer walls 17a, 17b, 17c together for strengthening the supporting element 17.

The upper wall 17a forms a smooth supporting surface, higher that the upper ends 12a of the chimneys 12. The two upper walls 17a form second supporting surfaces that define a first plane spaced apart from a second plane defined by said upper ends 12a of said chimneys 12, the distance between said first plane and said second plane being superior to the thickness of the flanges of the containers 2.

Figure 7:
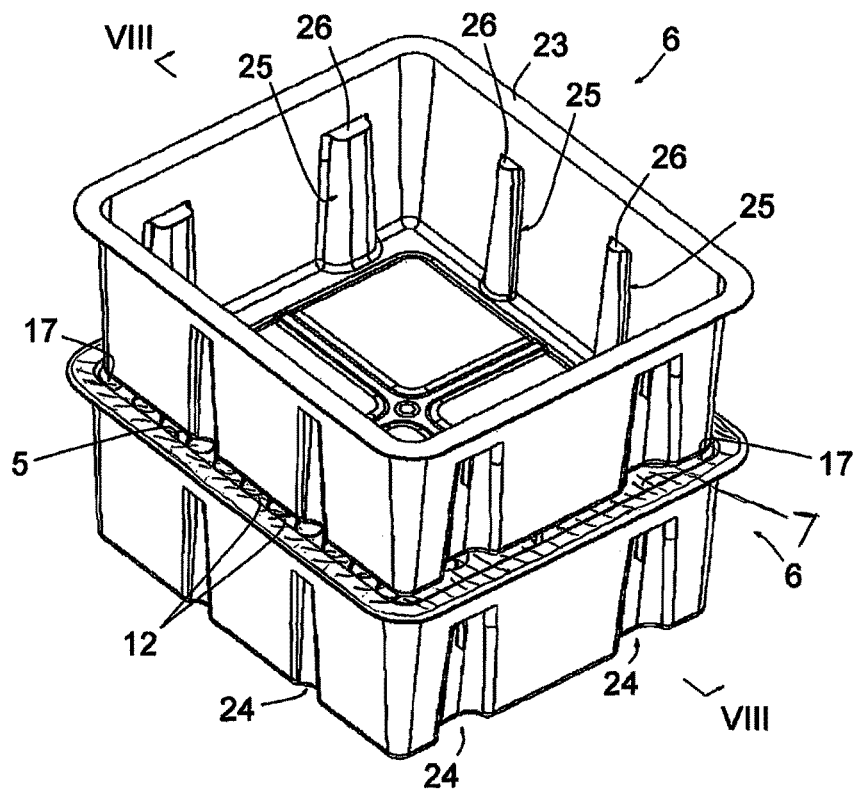
FIG. 7 is a view similar to FIG. 4, that is, a first tub, without nest, being stacked on a second tub with a nest therein.

The height of said upper wall 17a with respect to said upper ends 12a of said chimneys 12 is such that it is located, once the packaging 1 is constituted, at the level of the opening 22 of the tub 6, or just below this opening 22, as appearing on FIGS. 4, 7 and 8 and described below, and thus just below the sealing cover which this opening 22 receives.

Figure 4:
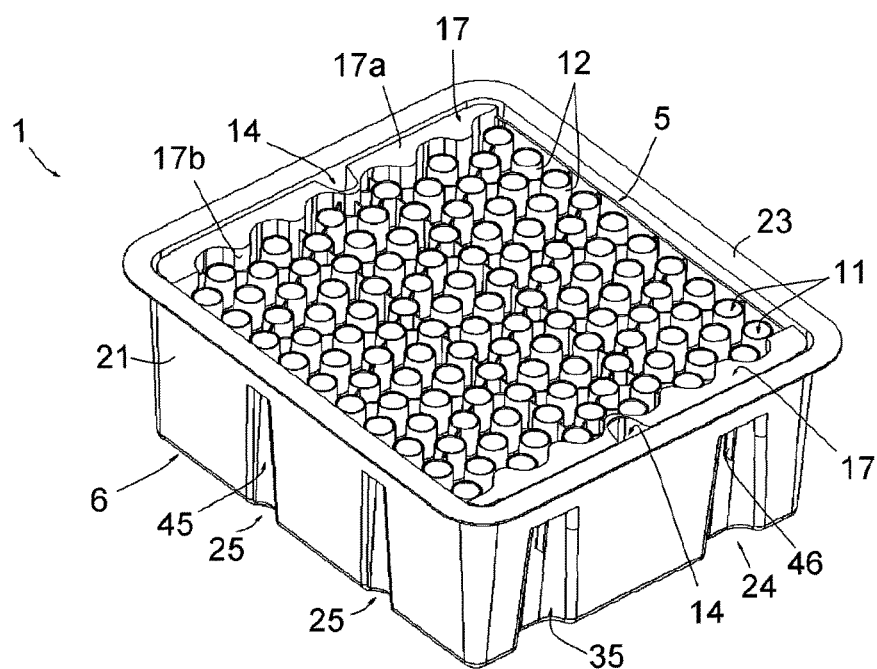
FIG. 4 is a top perspective view of the tub, another component of the packaging, with the nest therein.

As it can be seen on FIG. 4, when the nest 5, that comprises through openings 11 in order to receive the containers 2, is placed inside the tub 6, the second supporting surfaces 17 are in the same plane than the peripheral flange 23 of the tub 6.

Each said upper wall 17a exhibits an undulated inner edge, and said inner lateral wall 17b is undulated in the same manner. These walls 17a, 17b thus form successive alternated protruding portions and depressed portions that follow the outline of the successive chimneys 12 of the side row of chimneys, which said portion of the nest 5, comprises.

The upper faces of said protruding portions form grasping surfaces for suction cups intended to grasp the nest 5 along an automated handling process.

Figure 5:
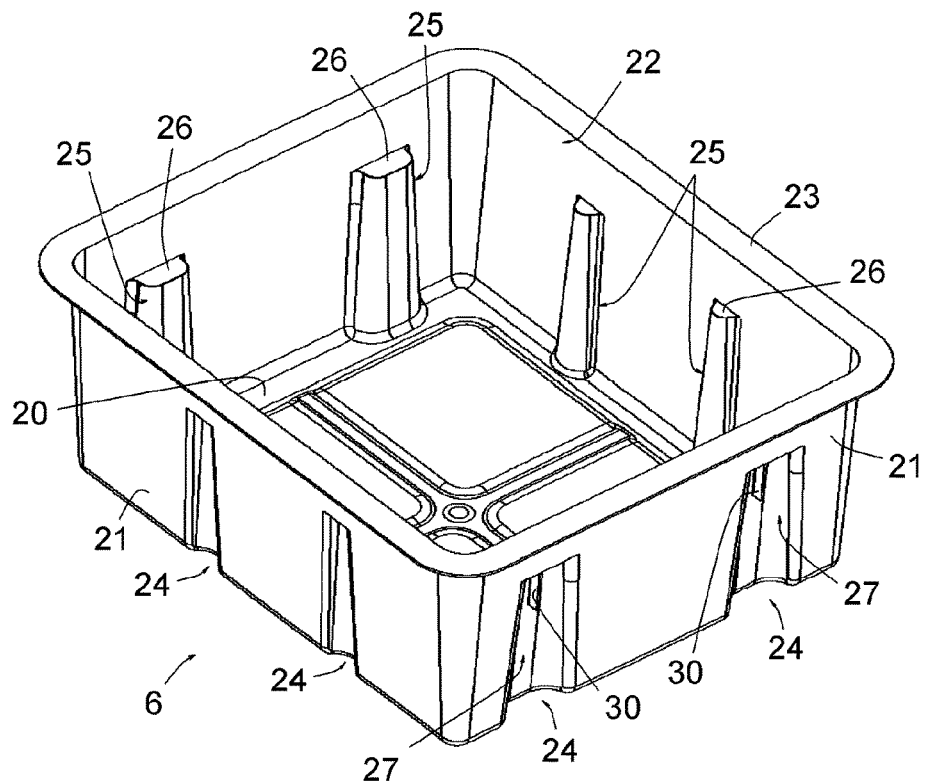
FIG. 5 is a top perspective view of the tub.
Figure 6:
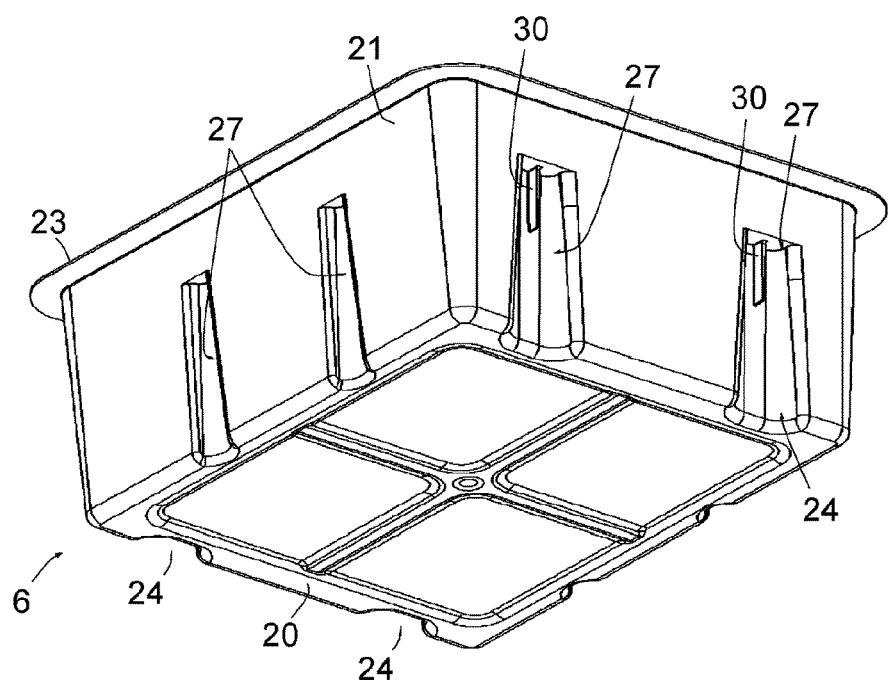
FIG. 6 is a perspective view of this tub, from below.

With reference to FIGS. 5 and 6, the tub 6 have a bottom wall 20, sloping lateral walls 21 forming an upper opening 22, a peripheral outer flange 23 levelled with this upper opening 22, and recessed portions 24. The tub 6 is formed by a single part of moulded plastic material.

Figure 9:
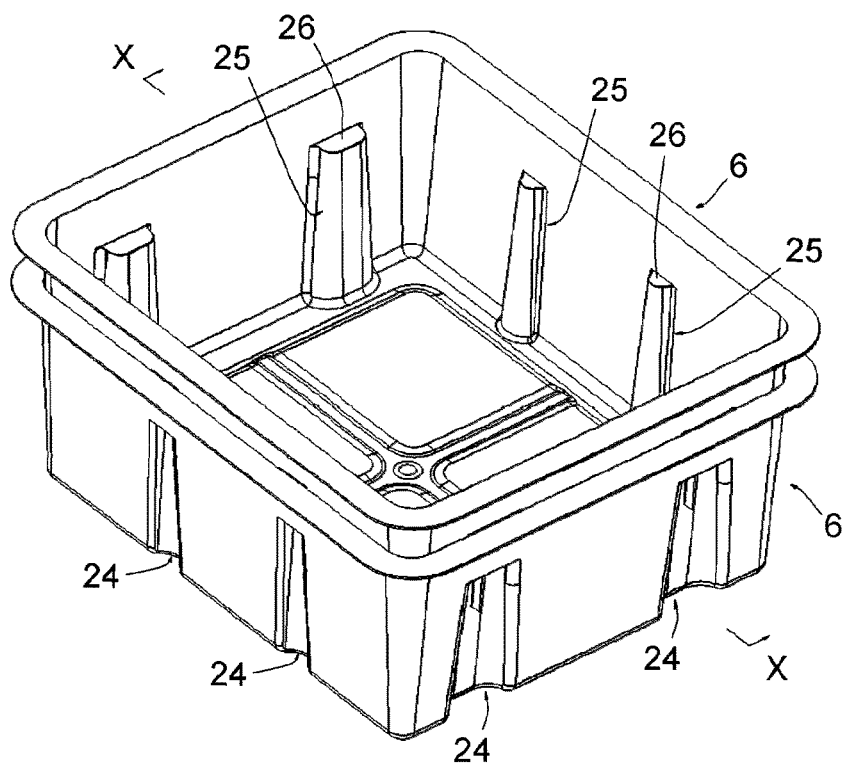
FIG. 9 is a view similar to FIG. 7, the first upper tub being nested in the second lower tub.
Figure 10:
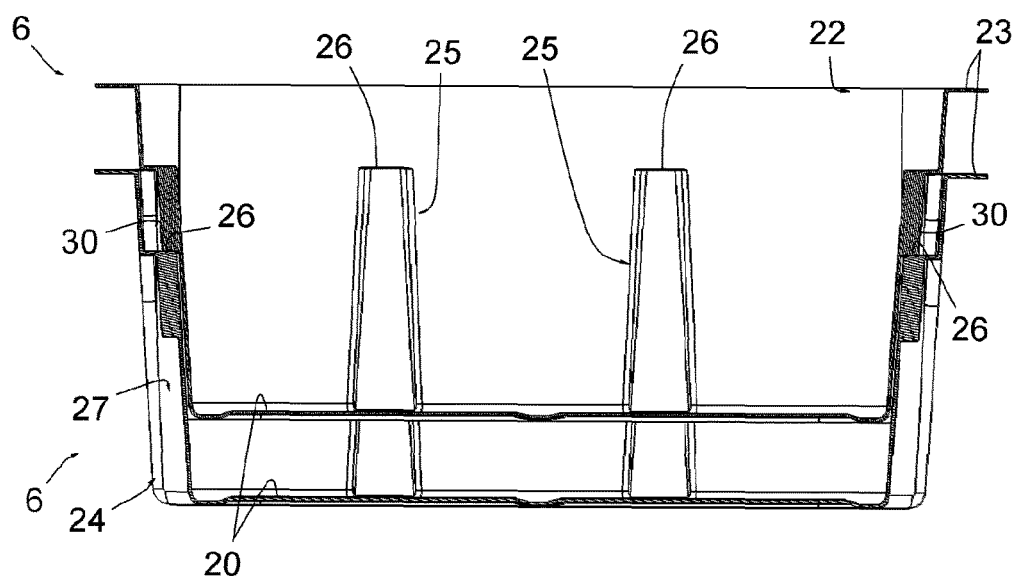
FIG. 10 is a cross-sectional view taken along line X-X of FIG. 9.

The lateral walls 21 are sloped inwardly from the opening 22 to the bottom wall 20, so that, as shown on FIGS. 9 and 10, when a first tub 6 is stacked on a second, identical, tub 6 having a nest 5 therein, the contour of the bottom wall 20 of said first tub 6 is within the contour of the opening 22 of said second tub 6. Said second supporting surfaces 17a are so located that the bottom wall 20 of said first tub 6 then bears thereon.

The peripheral outer flange 23 is intended to receive said sealing cover, sealed thereon.

Each recessed portion 24 forms, on the inner side of the wall 21, a supporting pillar 25 extending from the bottom wall 20 and forming an upper bearing surface 26 for receiving the nest 5. Each pillar 25 tapers off from the bottom wall 20 to this upper bearing surface 26, and the latter is located at a distance from the opening 22 which is slightly greater than the overall height of the supporting elements 17, i.e. the width of the walls 17c. On the outer side of the wall 21, each recessed portion 24 forms a recess 27 able to receive a corresponding supporting pillar 25 of said second tub 6.

Each recess 27 extends from the level of the bottom wall 20 up to the downward surface of the upper wall forming said upper bearing surface 26, and generally tapers off from this bottom wall 20 to this downward surface. The recesses 27 of two opposed walls 21 includes therein a median limiting bar 30 forming a lower abutting end. As shown on FIG. 10, in the nested position of the tubs 6, the median limiting bar 30 of the upper tub 6 abuts said upper bearing surface 26, thus forming limitation means for limiting the depth of nesting of one tub 6 in another to avoid any risk of blocking a tub 6 in the other.

The sealing cover 7 is formed by a sheet of suitable heat sealable material, in particular by a sheet made of Tyvek® (material sold by Dupont De Nemours Company), and is sealed on the outer flange 23 of the tub 6.

In use, the tubs 6 can be nested as shown on FIGS. 9 and 10, which provide an advantageous space saving for the manufacturer or user of the containers 2. After putting the nest 5 in the tubs 6, a large number of packagings 1 can be stacked without any risk of contamination or breakage of the flanges of the containers 2, the supporting elements 17 supporting the sealing covers and distributing the load of upper tubs in the stack on the lateral walls 21 of lower tubs of this stack.

For the user of the containers 2, the packagings 1, once extracted from the transporting cardboard boxes, can be stacked temporarily, also without any risk of contamination or breakage of the flanges of the containers 2, as shown on FIG. 4. After removal of the nests 6 therefrom, the packagings 1 can be nested and thus also provides an advantageous space saving for this user when nested.

As it has become evident from the foregoing, the invention provides a packaging for containers, having, in comparison with the packagings of the prior art, the following determining advantages of: (a) efficiently preventing any contamination or breakage of the containers when a number of tubs are stacked, (b) allowing packagings to be stacked, (c) reducing the necessary amount of materials for transporting the packagings, and (d) reducing the necessary work for opening the boxes containing these packagings.

The invention has been described above with references to embodiments given as examples. Obviously, the present invention is not limited to these embodiments and can be applied to all other embodiments covered by the appended claims.

The invention claimed is:

1. A packaging for containers each having a cylindrical body and an upper surface located at or near an extremity of the body, said packaging comprising a nest, a tub, and a sealing cover,
   the nest having nesting structure to receive the containers and comprising at least one first supporting surface, to be received on at least one corresponding supporting surface of the tub,
   the tub having a bottom wall, lateral walls forming an upper opening, and a peripheral flange levelled with said upper opening, for the sealing of said sealing cover thereon,
   wherein said nest comprises at least two second supporting surfaces on two opposed sides, each second supporting surface rigidly connected to said at least one first supporting surface, wherein the second supporting surfaces are wall surfaces, and are positioned with respect to the at least one first supporting surface so that the second supporting surface is located, when the nest is placed in the tub, at the level of said peripheral flange and wherein the second supporting surface is formed by an upper wall of a supporting element having an inner lateral wall and an outer lateral wall, wherein said supporting element comprises interior walls connecting said inner lateral wall and said outer lateral wall, for strengthening said supporting element,
   wherein the containers have flanges at their proximal ends and said nesting structure comprises chimneys in which the containers are intended to be inserted with the flanges thereof bearing on an upper end of said chimneys, said second supporting surfaces defining a first plane that is spaced apart from a second plane defined by said upper end of said chimneys, the distance between said first plane and said second plane being superior to the thickness of the flanges of the containers, and
   wherein the cover is configured to be sealed directly onto the peripheral flange after placement of the containers into the nest.

2. The packaging for containers according to claim 1, wherein said nesting structure comprises openings.

3. The packaging for containers according to claim 1, wherein said second supporting surface is integrally formed with the nest.

4. The packaging for containers according to claim 1, wherein said second supporting surface comprises additional pieces disposed on and/or attached to the nest.

5. The packaging for containers according to claim 1, wherein the nest has notches for the insertion of a user's fingers for grasping the nest.

6. The packaging for containers according to claim 5, wherein said notches are delimited by walls providing increased contact surfaces for the user's fingers.

7. The packaging for containers according to claim 5, wherein each notch has an abutment.

8. A packaging for containers each having a cylindrical body and an upper surface located at or near an extremity of the body, said packaging comprising a nest, a tub, and a sealing cover,
   the nest having nesting structure to receive the containers and comprising at least one first supporting surface, to be received on at least one corresponding supporting surface of the tub,
   the tub having a bottom wall, lateral walls forming an upper opening, and a peripheral flange levelled with said upper opening, for the sealing of said sealing cover directly thereon,
   wherein said nest comprises at least two second supporting surfaces on two opposed sides, each second supporting surface rigidly connected to said at least one first supporting surface, wherein the second supporting surfaces are wall surfaces, and are positioned with respect to the at least one first supporting surface so that the second supporting surface is located, when the nest is placed in the tub, at the level of said peripheral flange,
   wherein the containers have flanges at their proximal ends and said nesting structure comprises chimneys in which the containers are intended to be inserted with the flanges thereof bearing on an upper end of said chimneys, said second supporting surfaces defining a first plane that is spaced apart from a second plane defined by said upper end of said chimneys, the distance between said first plane and said second plane being superior to the thickness of the flanges of the containers, and
   wherein said lateral walls of the tub are sloped inwardly from said upper opening to said bottom wall, so that, when a first tub is stacked on a second, identical tub having a nest therein, a contour of the bottom wall of said first tub is within a contour of the upper opening of said second tub, and said second supporting surfaces are so located that the bottom wall of said first tub bears thereon.

9. A packaging for containers each having a cylindrical body and an upper surface located at or near an extremity of the body, said packaging comprising a nest, a tub, and a sealing cover,
   the nest having nesting structure to receive the containers and comprising at least one first supporting surface, to be received on at least one corresponding supporting surface of the tub,
   the tub having a bottom wall, lateral walls forming an upper opening, and a peripheral flange levelled with said upper opening, for the sealing of said sealing cover thereon,
   wherein said nest comprises at least two second supporting surfaces on two opposed sides, each second supporting surface rigidly connected to said at least one first supporting surface, wherein the second supporting surfaces are wall surfaces, and are positioned with respect to the at least one first supporting surface so that the second supporting surface is located, when the nest is placed in the tub, at the level of said peripheral flange,
   wherein the containers have flanges at their proximal ends and said nesting structure comprises chimneys in which the containers are intended to be inserted with the flanges thereof bearing on an upper end of said chimneys, said second supporting surfaces defining a first plane that is spaced apart from a second plane defined by said upper end of said chimneys, the distance between said first plane and said second plane being superior to the thickness of the flanges of the containers, and wherein the second supporting surface comprises a smooth part that is sized and shaped to form a gripping surface for receiving a tool able to grasp automatically the nest.

10. The packaging for containers according to claim 1, wherein the second supporting surfaces are undulating wall surfaces which correspond to an outline of a side portion of successive chimneys positioned adjacent thereto.

11. The packaging for containers according to claim 1, wherein the corresponding surface of the tub comprises at least one supporting pillar extending from a bottom wall of the tub and forming an upper bearing surface configured for receiving the nest.

12. The packaging for containers according to claim 11, wherein the at least one supporting pillar comprises a recessed portion extending from a lateral wall of the tub and a protrusion extending in an inward direction with respect to the lateral wall of the tub.

13. The packaging for containers according to claim 12, wherein the protrusion of at least one supporting pillar is configured for cooperating with a recess in the recessed portion of an adjacently disposed tub for nesting of the tubs upon removal of the nest.

14. The packaging of claim 1, wherein the inner lateral wall of the second supporting surface is located on a side adjacent the nest comprising the chimneys and the outer lateral wall is located on a side adjacent to the tub.

15. The packaging of claim 1, wherein the inner and outer lateral walls extend in a parallel direction with respect to each other.

16. The packaging of claim 15, wherein a space is located between the inner and outer lateral walls.

17. The packaging of claim 1, wherein the second supporting surface comprises a horizontally disposed top wall having a vertically disposed inner lateral wall and a vertically disposed outer lateral wall extending in a downwardly direction from the top wall and wherein a space is provided between the inner lateral wall and the outer lateral wall.

* * * * *